(12) United States Patent
Holeyannavar et al.

(10) Patent No.: US 11,353,381 B1
(45) Date of Patent: Jun. 7, 2022

(54) PORTABLE DISC TO MEASURE CHEMICAL GAS CONTAMINANTS WITHIN SEMICONDUCTOR EQUIPMENT AND CLEAN ROOM

(71) Applicant: Applied Materials, Inc., Santa Clara, CA (US)

(72) Inventors: Devendra Channappa Holeyannavar, Bangalore (IN); Dean C. Hruzek, Santa Clara, CA (US); Arunkumar Ramachandraiah, Karnataka (IN); Jeffrey C. Hudgens, San Francisco, CA (US); Shivaraj Manjunath Nara, Bangalore (IN); Paul B. Reuter, Austin, TX (US)

(73) Assignee: Applied Materials, Inc., Santa Clara, CA (US)

( * ) Notice: Subject to any disclaimer, the term of this patent is extended or adjusted under 35 U.S.C. 154(b) by 0 days.

(21) Appl. No.: 16/946,195

(22) Filed: Jun. 9, 2020

(51) Int. Cl.
  *G01N 1/24* (2006.01)
  *H05K 1/18* (2006.01)
  (Continued)

(52) U.S. Cl.
  CPC .............. *G01N 1/24* (2013.01); *G01N 1/04* (2013.01); *G01N 1/10* (2013.01); *G01N 1/20* (2013.01);
  (Continued)

(58) Field of Classification Search
  CPC .......... G01N 1/20; G01N 1/10; G01N 1/2035; G01N 1/04; G01N 27/12; G01N 1/24;
  (Continued)

(56) References Cited

U.S. PATENT DOCUMENTS 3,950,980 A * 4/1976 Braun ...................... G01N 7/10
  73/31.05
4,164,862 A * 8/1979 Jackson ............. G01N 33/0031
  73/25.03
(Continued)

FOREIGN PATENT DOCUMENTS

EP      2977973 A1    1/2016
JP   2004340945    * 12/2004   ............. G01N 27/04
(Continued)

OTHER PUBLICATIONS

Euro-Gas Management Services, Micro SS Sensor Solid State Multi-Gas/VOC, gore.com/gas-sensors, Nov. 1998, 13 pages (Year: 1998).*
(Continued)

*Primary Examiner* — Clayton E. La Balle
*Assistant Examiner* — Kevin C Butler
(74) *Attorney, Agent, or Firm* — Lowenstein Sandler LLP

(57) ABSTRACT

A detector disc includes a disc body having a bottom disc and a top cover, the top cover including a first aperture. A sensor is disposed inside the disc body and positioned to be exposed to an external environment via the first aperture in the top cover. The solid state sensor is adapted to detect levels of chemical gas contaminants and output a detection signal based on detected levels of the chemical gas contaminants. A microcontroller is disposed on the PCB and adapted to generate measurement data from the detected levels of the chemical gas contaminants embodied within the detection signal. A wireless communication circuit is disposed on the PCB, the wireless communication circuit adapted to transmit the measurement data wirelessly to a wireless access point device.

20 Claims, 10 Drawing Sheets

(51) Int. Cl.
*H04W 4/38* (2018.01)
*G01N 1/22* (2006.01)
*G01N 1/28* (2006.01)
*G01N 27/12* (2006.01)
*G01N 1/20* (2006.01)
*G01N 1/10* (2006.01)
*G01N 1/04* (2006.01)

(52) U.S. Cl.
CPC .......... *G01N 1/2035* (2013.01); *G01N 1/2214* (2013.01); *G01N 1/286* (2013.01); *G01N 27/12* (2013.01); *H04W 4/38* (2018.02); *H05K 1/181* (2013.01); *G01N 2001/245* (2013.01); *H05K 2201/10151* (2013.01)

(58) Field of Classification Search
CPC ....... G01N 1/2214; H04W 4/38; H05K 1/181; H05K 2201/10151
See application file for complete search history.

(56) References Cited

U.S. PATENT DOCUMENTS

| | | | | |
|---|---|---|---|---|
| 4,169,369 A * | 10/1979 | Chang | H01C 17/12 | 73/31.06 |
| 4,200,607 A * | 4/1980 | Suzuki | G01N 35/025 | 422/64 |
| 4,271,357 A * | 6/1981 | Bradshaw | G01N 27/68 | 250/282 |
| 4,358,951 A * | 11/1982 | Chang | G01N 27/12 | 73/31.05 |
| 4,387,359 A * | 6/1983 | Tien | G01N 27/12 | 338/34 |
| 4,432,224 A * | 2/1984 | Typpo | G01N 33/0044 | 73/24.01 |
| 4,443,791 A * | 4/1984 | Risgin | G08B 29/24 | 340/634 |
| 4,457,161 A * | 7/1984 | Iwanaga | G01N 33/0031 | 340/634 |
| 4,542,640 A * | 9/1985 | Clifford | G01N 33/0031 | 422/98 |
| 4,563,249 A * | 1/1986 | Hale | G01N 27/4045 | 204/415 |
| 4,571,292 A * | 2/1986 | Liu | G01N 27/404 | 204/412 |
| 5,342,701 A * | 8/1994 | Miremadi | G01N 27/12 | 423/561.1 |
| 5,367,283 A * | 11/1994 | Lauf | G01N 27/12 | 338/307 |
| 5,451,920 A * | 9/1995 | Hoffheins | G01N 27/12 | 338/307 |
| 5,625,209 A * | 4/1997 | Appleton | G01N 27/12 | 257/253 |
| 5,659,127 A * | 8/1997 | Shie | G01N 27/12 | 338/334 |
| 5,675,070 A * | 10/1997 | Gelperin | G01N 33/0011 | 73/23.34 |
| 5,821,402 A * | 10/1998 | Okajima | C23C 16/46 | 73/23.2 |
| 5,841,021 A | 11/1998 | Casto et al. | | |
| 5,942,676 A * | 8/1999 | Potthast | G01N 27/12 | 73/31.06 |
| 5,969,231 A * | 10/1999 | Qu | G01N 27/4075 | 338/34 |
| 6,059,937 A * | 5/2000 | Koh | G01N 27/12 | 204/192.11 |
| 6,942,738 B1* | 9/2005 | Nelson | H01L 21/67754 | 134/33 |
| 6,997,040 B1* | 2/2006 | Lee | G01N 27/12 | 73/31.05 |
| 7,982,296 B2* | 7/2011 | Nuzzo | H01L 29/78681 | 257/679 |
| 8,646,311 B1* | 2/2014 | Moseley | G01N 27/125 | 73/31.06 |
| 8,683,847 B2* | 4/2014 | Moon | G01N 27/123 | 73/31.06 |
| 8,846,406 B1* | 9/2014 | Martin | G01N 27/12 | 436/149 |
| 9,011,670 B2* | 4/2015 | Bickford | G01N 27/333 | 205/789 |
| 9,322,768 B1* | 4/2016 | Carrieri | G01J 3/0224 | |
| 10,763,920 B2* | 9/2020 | Mikolajczak | A61B 5/0015 | |
| 11,054,347 B1* | 7/2021 | Gogoana | G01N 33/0047 | |
| 2003/0209404 A1* | 11/2003 | Davis | H01L 21/68707 | 198/345.3 |
| 2003/0217586 A1* | 11/2003 | Gouma | G01N 27/12 | 73/31.06 |
| 2004/0005715 A1 | 1/2004 | Schabron et al. | | |
| 2004/0035183 A1* | 2/2004 | O'Brien | G01N 1/2202 | 73/23.27 |
| 2004/0211667 A1* | 10/2004 | Sberveglieri | G01N 27/12 | 204/426 |
| 2006/0154414 A1* | 7/2006 | Lin | G01N 21/78 | 438/222 |
| 2006/0234621 A1* | 10/2006 | Desrochers | F24F 3/044 | 454/239 |
| 2006/0240245 A1* | 10/2006 | Ishida | G01N 27/12 | 428/312.6 |
| 2007/0147976 A1* | 6/2007 | Rice | B25J 11/008 | 414/217 |
| 2007/0147982 A1* | 6/2007 | Rice | H01L 21/67178 | 414/800 |
| 2008/0032426 A1* | 2/2008 | Michaelson | H01L 22/20 | 438/7 |
| 2009/0074612 A1* | 3/2009 | Gross | G01N 7/02 | 422/400 |
| 2010/0086439 A1* | 4/2010 | Yamanaka | G01N 21/77 | 422/52 |
| 2010/0116691 A1* | 5/2010 | Papadimitrakopoulos | G01N 33/6803 | 205/778 |
| 2010/0206049 A1* | 8/2010 | Kasama | G01N 27/226 | 73/31.06 |
| 2010/0288014 A1* | 11/2010 | Yao | G01N 29/022 | 73/24.06 |
| 2011/0126515 A1* | 6/2011 | Saruhan-Brings | G01N 27/12 | 60/274 |
| 2011/0138880 A1* | 6/2011 | Jones | G01N 27/12 | 73/31.06 |
| 2011/0184657 A1* | 7/2011 | Chou | B82Y 15/00 | 702/24 |
| 2012/0119315 A1* | 5/2012 | Ou | G01N 27/12 | 257/431 |
| 2012/0293796 A1* | 11/2012 | Ludowise | B01L 3/5027 | 356/244 |
| 2013/0219995 A1* | 8/2013 | Dutta | G01N 27/129 | 73/31.06 |
| 2014/0223997 A1* | 8/2014 | Gole | G01N 27/06 | 73/31.06 |
| 2014/0311221 A1* | 10/2014 | Gole | G01N 27/127 | 73/31.06 |
| 2015/0351648 A1* | 12/2015 | Harvey | A61B 5/076 | 600/561 |
| 2016/0370797 A1 | 12/2016 | Azarya et al. | | |
| 2017/0082586 A1* | 3/2017 | Williamson | G01N 15/10 | |
| 2017/0138879 A1* | 5/2017 | Akiyama | H01L 31/0272 | |
| 2017/0234820 A1* | 8/2017 | Lettow | G01M 3/18 | 422/82.02 |
| 2018/0140970 A1* | 5/2018 | Porter | B01D 15/12 | |
| 2018/0180573 A1* | 6/2018 | Lin | H01L 29/78684 | |
| 2019/0003997 A1* | 1/2019 | Noguchi | G01N 15/0606 | |
| 2019/0004020 A1* | 1/2019 | Dobrokhotov | G01N 33/0031 | |
| 2019/0025264 A1 | 1/2019 | Peng et al. | | |
| 2019/0086285 A1* | 3/2019 | Yoshino | G08B 21/20 | |
| 2019/0346390 A1* | 11/2019 | Lettow | G01N 27/12 | |
| 2020/0003746 A1* | 1/2020 | LeFiles | G01N 33/0029 | |
| 2020/0033283 A1* | 1/2020 | Nakao | G01N 27/126 | |

(56) References Cited

U.S. PATENT DOCUMENTS

| | | | |
|---|---|---|---|
| 2020/0132630 A1* | 4/2020 | Lee | G01N 29/036 |
| 2020/0394886 A1* | 12/2020 | Antar | G01N 15/06 |
| 2020/0400599 A1* | 12/2020 | Wienecke | G01N 27/12 |

FOREIGN PATENT DOCUMENTS

| | | | | |
|---|---|---|---|---|
| WO | 8501351 A1 | 3/1985 | | |
| WO | WO-8501351 A1 * | 3/1985 | | G01N 33/0031 |
| WO | WO-2008084582 A1 * | 7/2008 | | G01N 27/12 |
| WO | 2016044711 A1 | 3/2016 | | |
| WO | 2020005431 | 1/2020 | | |

OTHER PUBLICATIONS

Gerhard Müller et al., Solid-State Gas Sensors: Sensor System Challenges in the Civil Security Domain, Materials 2016, 9, 65; doi: 10.3390/ma9010065, 30 pages (Year: 2016).*

P T Moseley, Solid state gas sensors, Measurement Science and Technology 8, 1997, 223-237 pages (Year: 1997).*

"Micron SS Sensor Solid State Multi-Gas / VOC," Euro-Gas Management Services Ltd., www.euro-gasman.com, 4 pages.

PCT Notification of Transmittal of The International Search Report and The Written Opinion Of The International Searching Authority for PCT Application No. PCT/US2021/036356, dated Sep. 27, 2021, 10 pages.

* cited by examiner

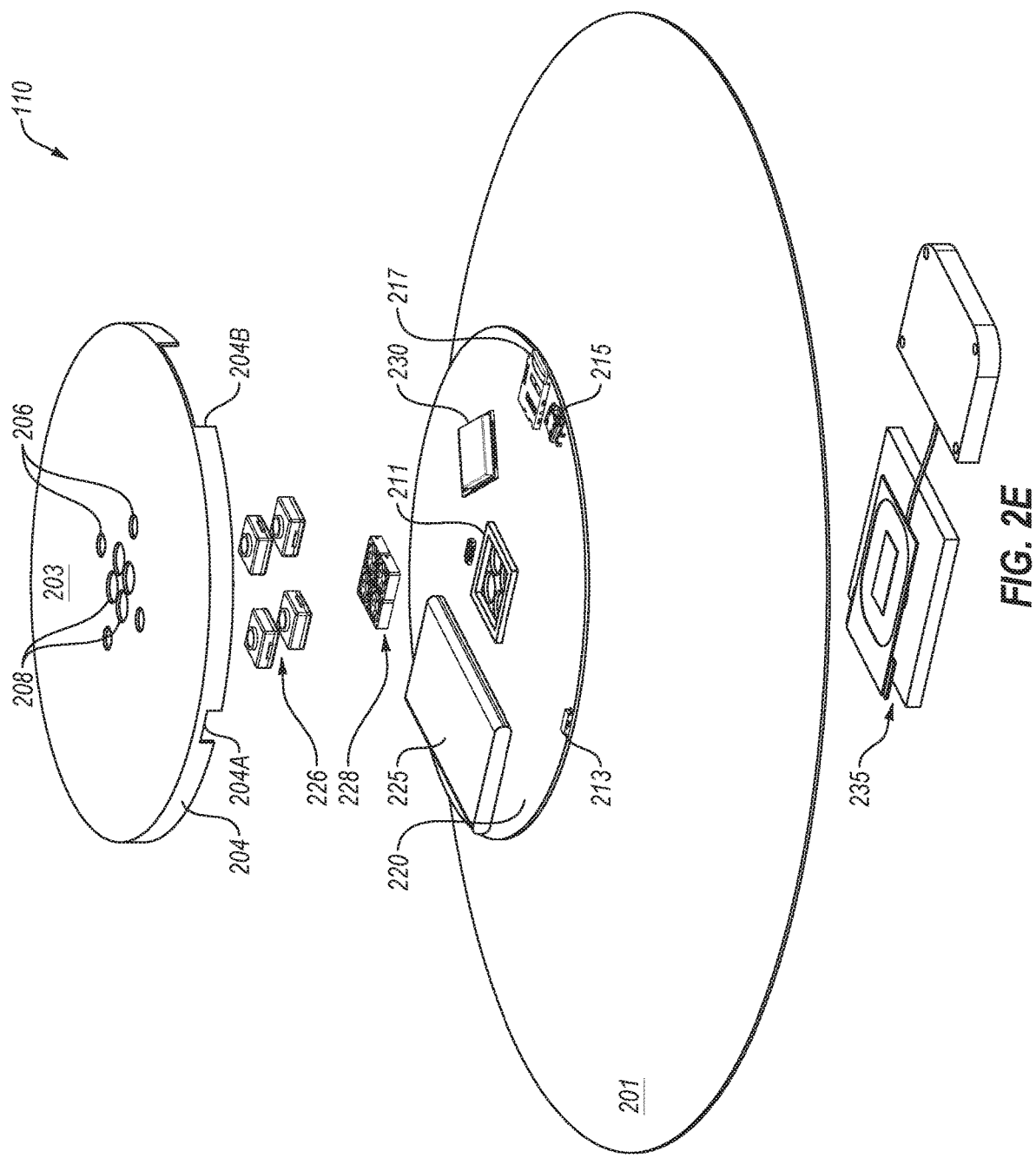

PORTABLE DISC TO MEASURE CHEMICAL GAS CONTAMINANTS WITHIN SEMICONDUCTOR EQUIPMENT AND CLEAN ROOM

TECHNICAL FIELD

Some embodiments of the present invention relate, in general, to a portable disc to measure chemical gas contaminants within semiconductor equipment and/or clean rooms.

BACKGROUND

For years, the main focus for semiconductor equipment, clean room, and other such clean fabrication ("fab") environments has been to remove mechanical particles from the air known to cause defects in thin films laid down for processing, and thus reduce the number of defects or errors in semiconductor manufactured devices. More recently, this focus has expanded to the reduction of chemical gas contaminants generally referred to as airborne molecular contaminants (AMCs) and volatile organic compounds (VOCs). For example, fabs have begun using chemical pre-filters to filter already filtered air in the fab level to filter even more at the processing tool level. Process manufacturers have begun to change manufacturing processes to clean vacuum parts to ensure small trace amounts of chemical gas contaminants do not make it into the production environment. These are not inexpensive measures, and despite these efforts, the complexity of semiconductor processing system tools makes it difficult to determine where in a multi-step, multi-tool process substrates may be getting exposed to too high a concentration of any number of chemical gas contaminants.

SUMMARY

Some embodiments described herein cover a detector disc including a disc body comprising a bottom disc and a top cover, the top cover comprising a first aperture. The detector disc may further include a printed circuit board (PCB) positioned within an interior formed by the disc body. The detector disc may further include a sensor disposed on the PCB and positioned to be exposed to an external environment via the first aperture in the top cover. The sensor may be adapted to detect levels of chemical gas contaminants and output a detection signal based on detected levels of the chemical gas contaminants. The detector disc may further include a microcontroller disposed on the PCB and coupled to the sensor, the microcontroller adapted to generate measurement data from the detected levels of the chemical gas contaminants embodied within the detection signal. The detector disc may further include a wireless communication circuit disposed on the PCB, the wireless communication circuit adapted to transmit the measurement data wirelessly to a wireless access point device.

In other embodiments, the detector disc instead includes a substrate disc and a printed circuit board (PCB) disposed on a central portion of the substrate disc. The detector disc may further include a sorbent tube attached to the substrate disc, the sorbent tube comprising a first opening at a first end that is capped and a second opening at a second end. The detector disc may further include a micro-electromechanical system (MEMS) pump disposed on one of the substrate disc or the PCB and including an air tube attached to the second opening of the sorbent tube to force ambient air into the sorbent tube, wherein the MEMS pump is to automatically shut off after a calibrated time period after activation. The detector disc may further include a microcontroller disposed on the PCB and coupled to the MEMS pump, the microcontroller to activate the pump.

In example embodiments, a method is disclosed for using a detector disc for detecting levels of chemical gas contaminants in air. The method may begin with moving, by a first robot, the detector disc from a storage location through a factory interface into a load lock of a processing system. The detector disc may include a sensor adapted to detect levels of chemical gas contaminants in air; and a wireless communication circuit coupled to the sensor The method may continue with moving, by a second robot, the detector disc from the load lock through a transfer chamber and into a processing chamber of the processing system. The method may continue with detecting, using the sensor of the detector disc, the levels of chemical gas contaminants within at least one of the storage location, the factory interface, the load lock, the transfer chamber, or the processing chamber. The method may continue with transmitting, with the wireless communication circuit of the detector disc, measurement data wirelessly to a wireless access point (WAP) device, wherein the measurement data comprises information indicative of the detected levels of chemical gas contaminants within the at least one of the storage location, the factor interface, the load lock, the transfer chamber, or the processing chamber.

BRIEF DESCRIPTION OF THE DRAWINGS

The present invention is illustrated by way of example, and not by way of limitation, in the figures of the accompanying drawings in which like references indicate similar elements. It should be noted that different references to "an" or "one" embodiment in this disclosure are not necessarily to the same embodiment, and such references mean at least one.

FIG. 2E is an exploded, perspective view of the detector disc according aspects of the disclosure.

DETAILED DESCRIPTION OF EMBODIMENTS

Figure 1:
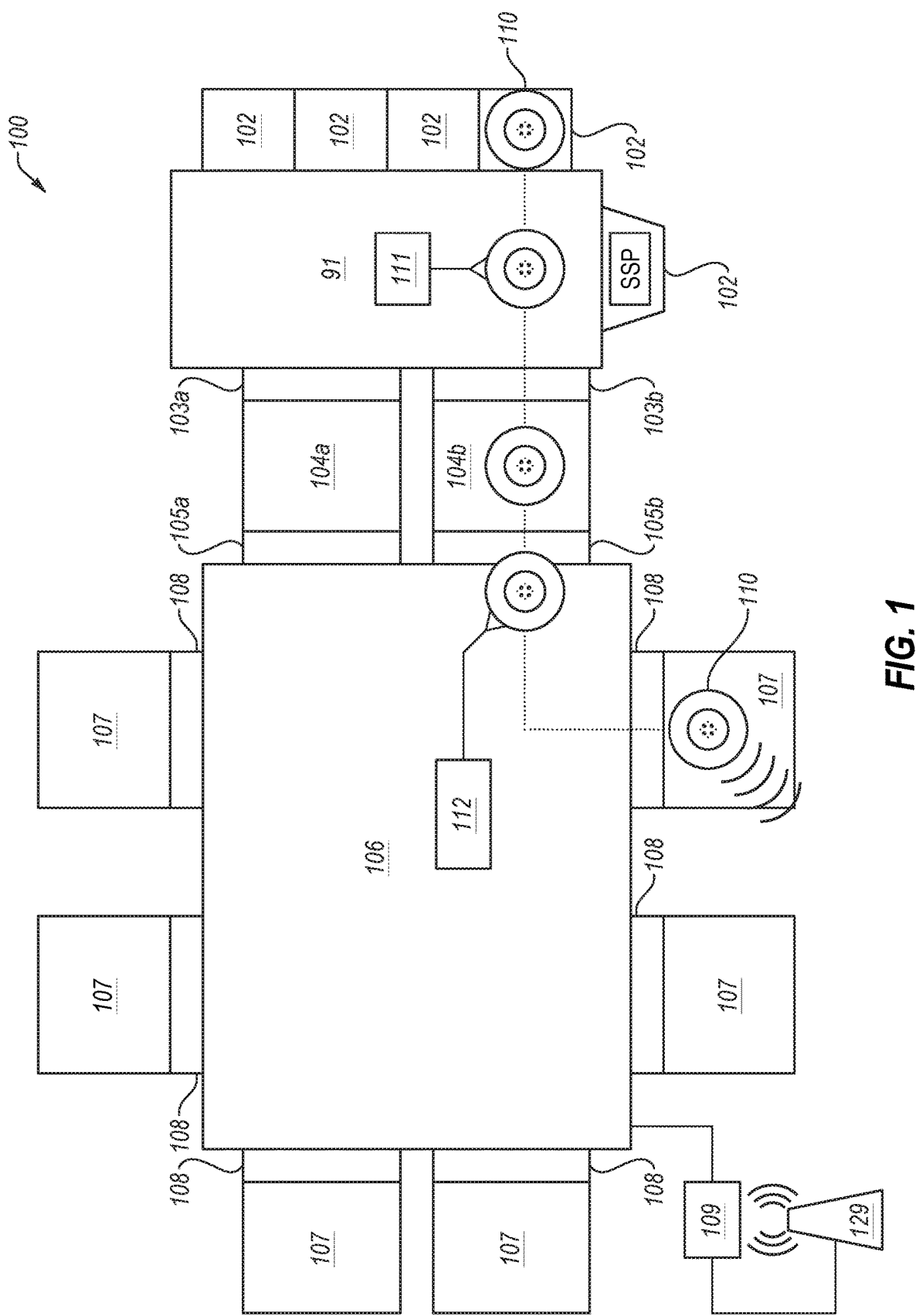
FIG. 1 is a simplified top view of an example processing system, according to aspects of the disclosure.

Embodiments of the present disclosure provide a detector disc and related methods for detecting levels of chemical gas contaminants within semiconductor processing equipment, fabrication, and clean room environments. The chemical gas contaminants may include levels of different types of airborne molecular contaminants (AMCs) and/or volatile organic compounds (VOCs). The disclosed embodiments provide a way to detect these chemical gas contaminants within a known part of a processing system, whether in a storage location for substrates, in a load lock or other intermediate station, a transfer chamber, or a processing chamber or the like.

Various embodiments may be or employ a detector disc that is of a thickness and diameter that the detector disc can be transferred as any other substrate through the processing system. In one embodiment, the detector disc includes a solid state sensor adapted to, while being transferred within the processing system, detect levels (e.g., down to less than two parts per million) of different chemical gas contaminants and output a detection signal based on the detected levels. A microcontroller coupled to the solid state sensor generates measurement data from the detected levels of the chemical gas contaminants embodied within the detection signal. A wireless communication circuit wirelessly transfers the detected levels to a wireless access point (WAP) device for capture. In related embodiments, the measurement data is stored in memory of the detector disc for later extraction, and thus may not have wireless capability in some environments. The measurement data is correlated with position of the detector disc within the processing system, and thus provide information about the detected levels of the chemical gas contaminants separately within a storage location, a factory interface, a load lock, a transfer chamber, or a processing chamber, to name a few.

In an alternative embodiment, the detector disc instead employs one or more sorbent tube attached to a substrate disc, and a micro-electromechanical system (MEMS) pump is adapted to force ambient air into the sorbent tube. A microcontroller activates the MEMS pump upon movement (or some other trigger) and the MEMS pump automatically shuts off after a calibrated time period after activation or responsive to a shutoff signal. The shut off of the MEMS pump traps the ambient air in the sorbent tube, so that after the detector disc is transferred back out of the processing system, the sorbent tube can be capped and transferred to an analysis lab. The sorbent tube is processed using gas chromatography to determine the levels of chemical gas contaminants in the sorbent tube. While this embodiment may be slower, use of sorbent tubes and gas chromatography can yield more accurate results.

These and similar embodiments provide a number of advantages and improvements in the field of semiconductor processing of substrates such as wafers. These advantages include an improvement in substrate performance (e.g., yield) and in a lower cost of ownership due to increased yields. Substrate manufacturing performance can be increased, for example, due to knowing where ambient air has too high a level of different kinds of chemical gas contaminants and targeting additional chemical gas filtration in these areas or tools. Furthermore, the monitoring of the levels of chemical gas contaminants may be continuous and substrate processing need not be shut down to detect and address certain high level concentrations in certain semiconductor processing tools or fab areas.

FIG. 1 illustrates a simplified top view of an example processing system 100, according to one aspect of the disclosure. The processing system 100 includes a factory interface 91 to which a plurality of substrate cassettes 102 (e.g., front opening unified pods (FOUPs) and a side storage pod (SSP)) may be coupled for transferring substrates (e.g., wafers such as silicon wafers) into the processing system 100. The FOUP, SSP, and other substrate cassettes may together be referred to herein as storage locations. In embodiments, one or more of the substrate cassettes 102 include, in addition to or instead of wafers to be processed, detector discs 110. Detector discs 110 may be used to detect levels of chemical gas contaminants within one or more processing chamber 107 and other compartments and chambers as will be discussed. The factory interface 91 may also transfer the detector discs 110 into and out of the processing system 100 using the same functions for transferring wafers as will be explained.

The processing system 100 may also include first vacuum ports 103a, 103b that may couple the factory interface 91 to respective stations 104a, 104b, which may be, for example, degassing chambers and/or load locks. Second vacuum ports 105a, 105b may be coupled to respective stations 104a, 104b and disposed between the stations 104a, 104b and a transfer chamber 106 to facilitate transfer of substrates into the transfer chamber 106. The transfer chamber 106 includes multiple processing chambers 107 (also referred to as process chambers) disposed around the transfer chamber 106 and coupled thereto. The processing chambers 107 are coupled to the transfer chamber 106 through respective ports 108, such as slit valves or the like.

The processing chambers 107 may include one or more of etch chambers, deposition chambers (including atomic layer deposition, chemical vapor deposition, physical vapor deposition, or plasma enhanced versions thereof), anneal chambers, and the like. In various embodiments, the factory interface 91 includes a factory interface robot 111. The factory interface robot 111 may include a robot arm, and may be or include a selective compliance assembly robot arm (SCARA) robot, such as a 2 link SCARA robot, a 3 link SCARA robot, a 4 link SCARA robot, and so on. The factory interface robot 111 may include an end effector on an end of the robot arm. The end effector may be configured to pick up and handle specific objects, such as wafers. Alternatively, the end effector may be configured to handle objects such as the detector discs 110. The factory interface robot 111 may be configured to transfer objects between substrate cassettes 102 (e.g., FOUPs and/or SSP) and stations 104a, 104b.

The transfer chamber 106 includes a transfer chamber robot 112. The transfer chamber robot 112 may include a robot arm with an end effector at an end of the robot arm. The end effector may be configured to handle particular objects, such as wafers, edge rings, ring kits, and detector discs. The transfer chamber robot 112 may be a SCARA robot, but may have fewer links and/or fewer degrees of freedom than the factory interface robot 111 in some embodiments.

A controller 109 may control various aspects of the processing system 100 and may include or be coupled to a wireless access point (WAP) device 129. The WAP device 129 may include wireless technology and one or more antenna with which to communicate with the detector discs 110. The controller 109 may be and/or include a computing device such as a personal computer, a server computer, a programmable logic controller (PLC), a microcontroller, and so on. The controller 109 may include one or more processing devices such as a microprocessor, central processing unit, or the like. More particularly, the processing device may be a complex instruction set computing (CISC) microprocessor, reduced instruction set computing (RISC) microprocessor, very long instruction word (VLIW) microprocessor, or a processor implementing other instruction sets or processors implementing a combination of instruction sets. The processing device may also be one or more special-purpose processing devices such as an application specific integrated circuit (ASIC), a field programmable gate array (FPGA), a digital signal processor (DSP), network processor, or the like.

Although not illustrated, the controller 109 may include a data storage device (e.g., one or more disk drives and/or solid state drives), a main memory, a static memory, a network interface, and/or other components. The controller 109 may execute instructions to perform any one or more of the methodologies and/or embodiments described herein. The instructions may be stored on a computer readable storage medium, which may include the main memory, static memory, secondary storage and/or processing device (during execution of the instructions). For example, the controller 109 may execute the instructions to activate one or more chemical gas filters that are located within the different storage locations, the factory interface 91, the load lock or stations, the transfer chamber 106, or in any of the processor chambers 107 in response to detection of elevated levels of chemical gas contaminants in any one of these processing tool units or chambers.

Figure 2A:
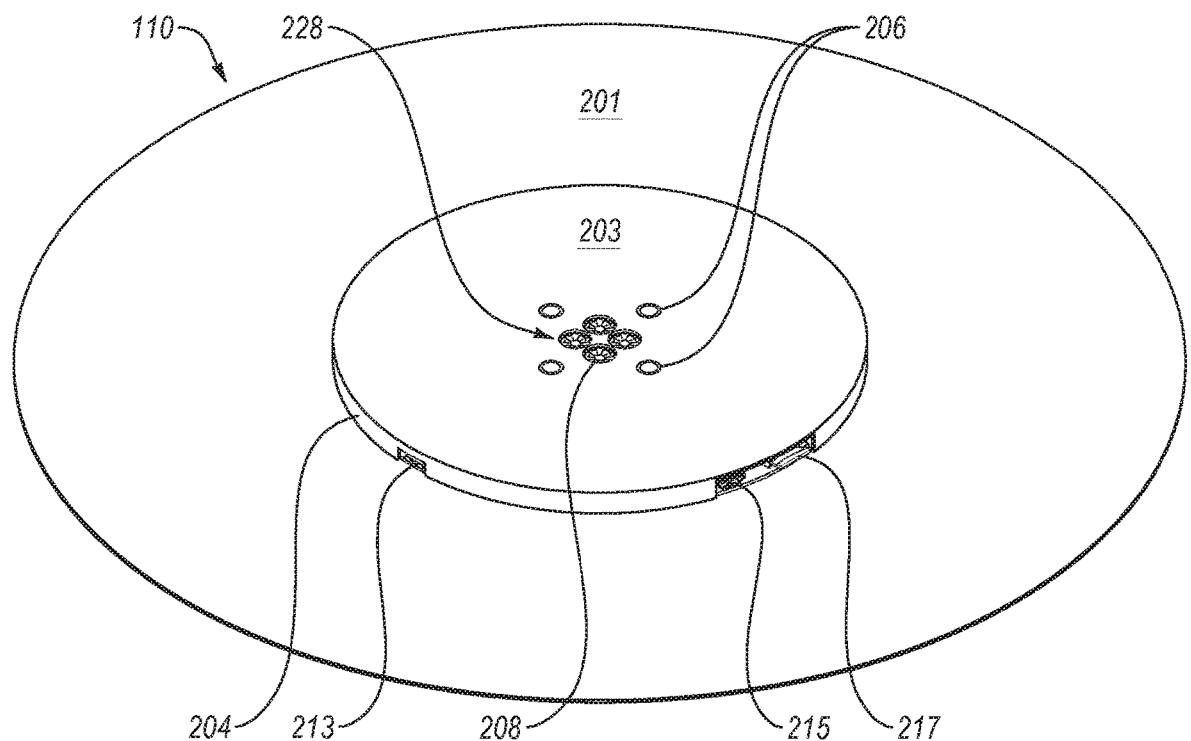
FIGS. 2A-2B are top, perspective views of a detector disc according to aspects of the disclosure.
Figure 2B:
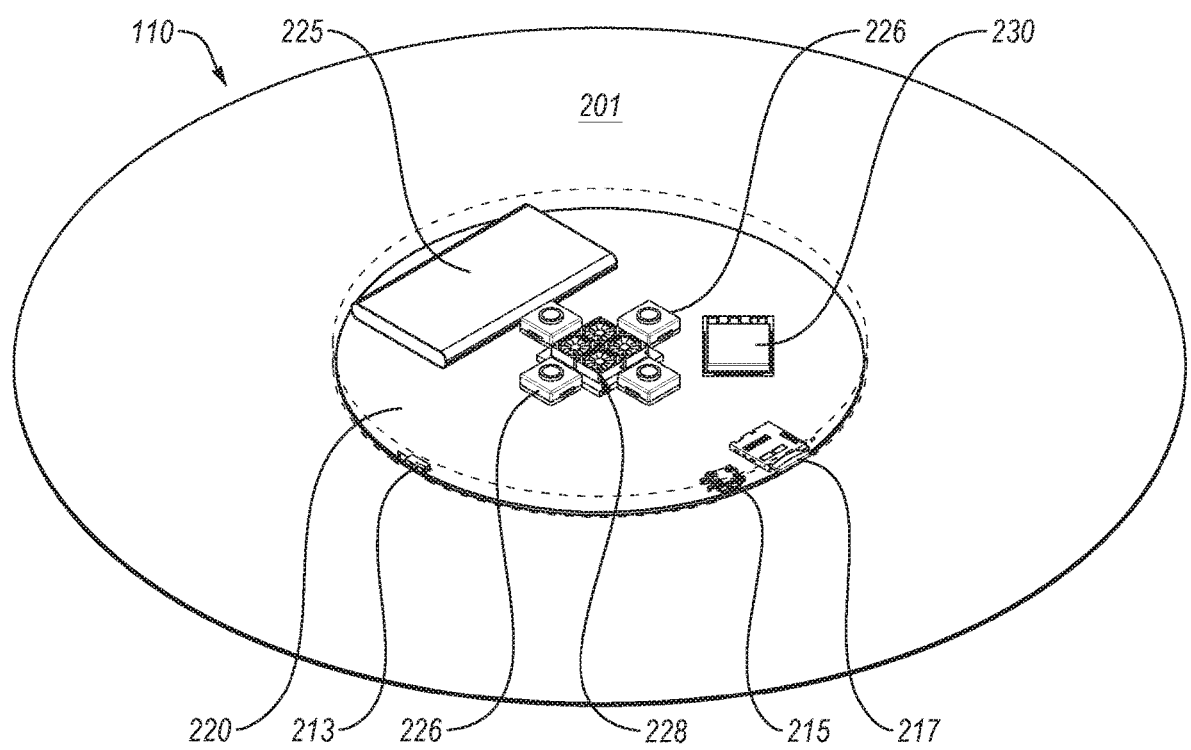
Figure 2C:
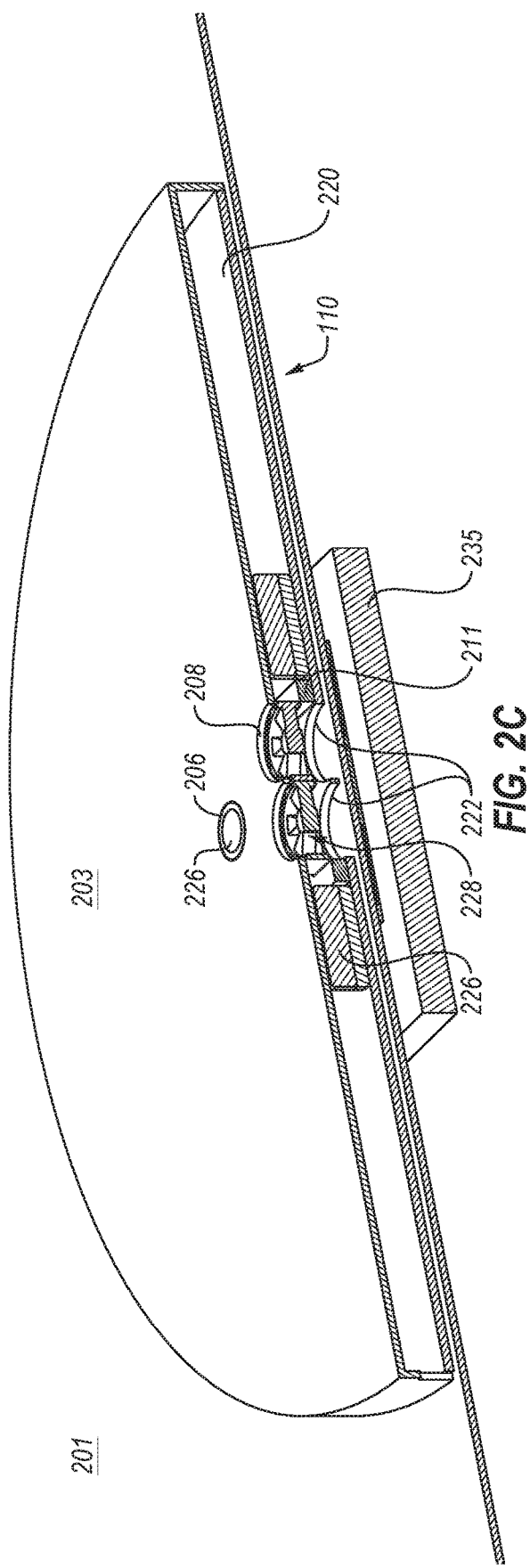
FIGS. 2C-2D are cross-section views along a center of the detector disc according to aspects of the disclosure.
Figure 2D:
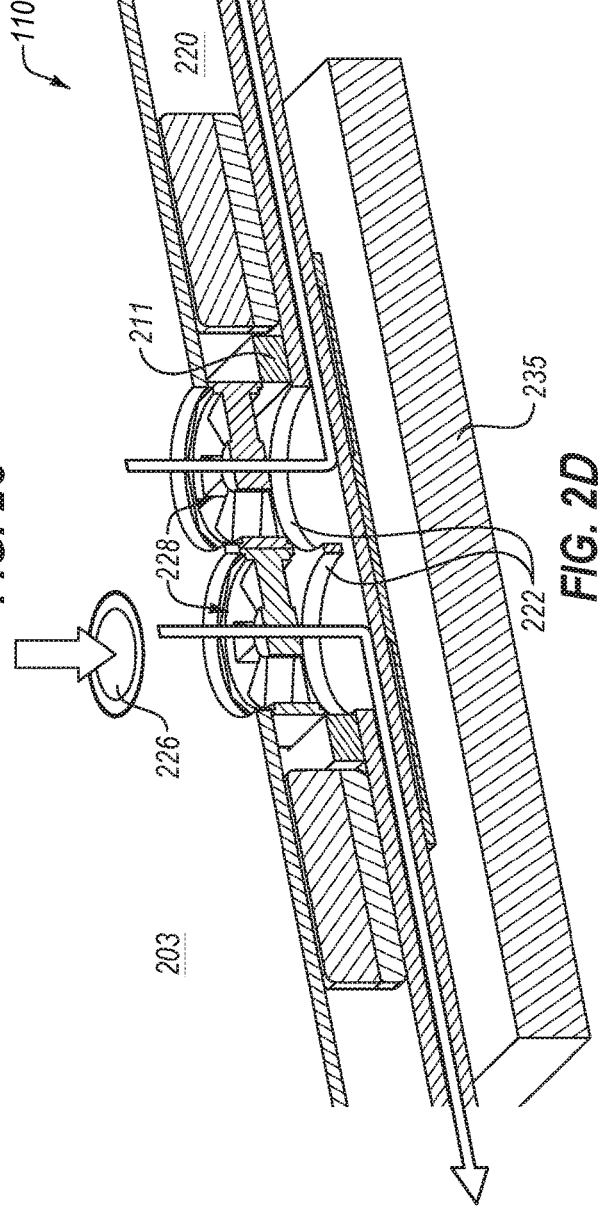

FIGS. 2A-2B are top, perspective views of the detector disc 110 according to aspects of the disclosure. FIGS. 2C-2D are cross-section views along a center of the detector disc 110 according to aspects of the disclosure. FIG. 2E is an exploded, perspective view of the detector disc 110 according aspects of the disclosure. In various embodiments, and with reference to these various views, the detector disc 110 includes a disc body that includes a substrate 201 and a top cover 203 having a sidewall 204 attached to the substrate 201. Alternatively, the substrate 201 may have side walls, and the top cover may be a lid that is disposed on the side walls of the substrate 201. In one embodiment, the substrate 201 includes a depression formed in the substrate 201. The top cover may be disposed over the depression. In one embodiment, the disc body is between 6 millimeters (mm) and mm thick and the diameter of the disc body (e.g., of the substrate 201) is approximately 190 mm to 320 mm and/or otherwise sized to be passed through slits and apertures of the processing system 100.

In various embodiments, the detector disc includes a printed circuit board (PCB) 220 positioned within an interior of the disc body, e.g., between the top cover 203 and the substrate 201. The sidewall 204 may enclose the PCB 220 within the disc body. A number of electrical components may be disposed inside of the disc body (e.g., on the PCB 220 or on a combination electronics boards), including a toggle on/off switch 213, a Universal Serial Bus (USB) interface connector 215, a memory card 217, a battery 225, one or more sensor 226, one or more axial fan 228, and a microcontroller 230. The one or more axial fan 228 may be disposed on the PCB 220 via a seal or bond. The one or more axial fan 228 facilitates air flow orthogonal to the one or more axial fan 228 without side leakage of the air. The battery 225 may power the electrical components that use power with the help of a power manager, discussed with reference to FIG. 4.

In disclosed embodiments, the microcontroller 230 is a controller adapted to interface with the electrical components, including the connectors, the memory card 217, and the one or more sensor 226. The microcontroller 230 may be a programmed processor, a field programmable gate array (FPGA), an application-specific integrated circuit (ASIC), or other special purpose processing device. The microcontroller 230 may be adapted to receive detection signals from the sensor 226 upon the sensor 226 detecting certain levels of concertation of chemical gas contaminants. The microcontroller 230 may also be configured or programed to generate measurement data from the detected levels of the chemical gas contaminants embodied within the detection signal. Functionality and capability of the microcontroller 230 will be discussed in more detail with reference to FIG. 4 and FIG. 6. In embodiments, the sensor 226 is a solid state sensor, an optical device, an electrochemical device, an electrical device, a mass sensitive device, a magnetic device, a thermometric device, or a combination thereof. The sensor 226 can be calibrated within air located outside the factory interface 91 that includes the storage location. The calibrating may include establishing a baseline of levels of the chemical gas contaminants detected by the one or more sensor 226.

In some embodiments, the sidewall 204 of the top cover 203 includes at least one opening, e.g., a first opening 204A through which the toggle on/off switch 213 is exposed and a second opening 204B through which the USB interface connector 215, and the memory card 217 are exposed. Additional or fewer openings may be employed depending on design. The memory card 217 may be removable and be adapted to store measurement data that includes the levels of concentration of different chemical gas contaminants that the sensor 226 is capable of detecting. A wireless charger 235 may also be provided that is adapted to wireless charge the detector disc 110.

In one embodiment, the sensor 226 is a micro solid state sensor adapted to detect the levels of chemical gas contaminants in parts per million (ppm) of particles of at least one of airborne molecular contaminants or volatile organic compounds, e.g., down to below two ppm and as high as 2000 ppm. In one embodiment, the micro solid state sensor is capable of detecting at least 23 different such chemical gases (AMCs and/or VOCs), e.g., ammonia ($NH_3$), carbon dioxide ($CO_2$), chlorine ($Cl_2$), hydrogen cyanide (HCN), Sulphur dioxide ($SO_2$), and many others. The micro solid state sensor may use amperometric, three-electrode advanced solid state technology in some embodiments.

In various embodiments, the sensor 226 is adapted to measure fifty percent of a concentration of the levels of the chemical gas contaminants within 10 seconds and measure ninety percent of the concentration of the levels of the chemical gas contaminants within 30 seconds. The sensor 226 may be about 12.5 mm by 11.5 mm by 9.5 mm in size, or within 5-20% of this size in various dimensions, and thus sized to allow multiple sensors to fit on the PCB 220 (e.g., illustrated are four sensors by way of example). The sensor 226 may also operate in a range in temperature between −20° C. and +50° C., and thus be adaptable to the processing chamber environment.

In various embodiments, the top cover 203 includes one or more first aperture 206 through which a detector surface of the one or more sensor 226 may be exposed to an external environment. The top cover 203 may also include one or more second aperture 208 that is proximate to the first aperture 206, through which the one more axial fan 228 can pull air from the external environment. The axial fan 228 may be disposed on the PCB 220 below the second aperture 208, such that the axial fan 228 moves the air across the sensor 226 disposed proximate to the axial fan 228. In an embodiment, the PCB 220 includes one or more third aperture 222 over which to dispose the one or more axial fan 228. In other words, the axial fan 228 can be disposed on the PCB 220 between the second and third apertures to move air across the sensor 226 in through the second aperture 208 and out through the third aperture 222 of the PCB 220.

In disclosed embodiments, the axial fan 228 moves air in this way to increase air flow and thus sensitivity, by the one or more sensor 226, to detection of the chemical gas contaminants, as illustrated by the direction of air flow (illustrated with arrows) in FIG. 2D. The microcontroller 230 may control the speed of the axial fan 228, e.g., via use of pulse width modulation (PWM) to vary the force of the air flow and therefore the sensitivity of the sensor 226.

In various embodiments, the top cover 203 includes a set of first apertures 206 (e.g., four first apertures) and the detector disc 110 includes a set of sensors 226 (e.g., four sensors) disposed on the PCB 220. Each sensor of the set of sensors may be positioned proximate to one of the set of first apertures 206. In a related embodiment, the top cover 203 includes a set of second apertures 208 (e.g., four second apertures) proximate to the set of first apertures 206. The PCB 220 may further include a set of third apertures 222 (e.g., four third apertures) positioned below the set of second apertures 208. The detector disc 110 may include a set of axial fans 228 disposed on the PCB 220 between the set of second apertures 208 and the set of third apertures 222. The set of axial fans 228 may move air across the set of sensors 226.

Figures 3A, 3B:
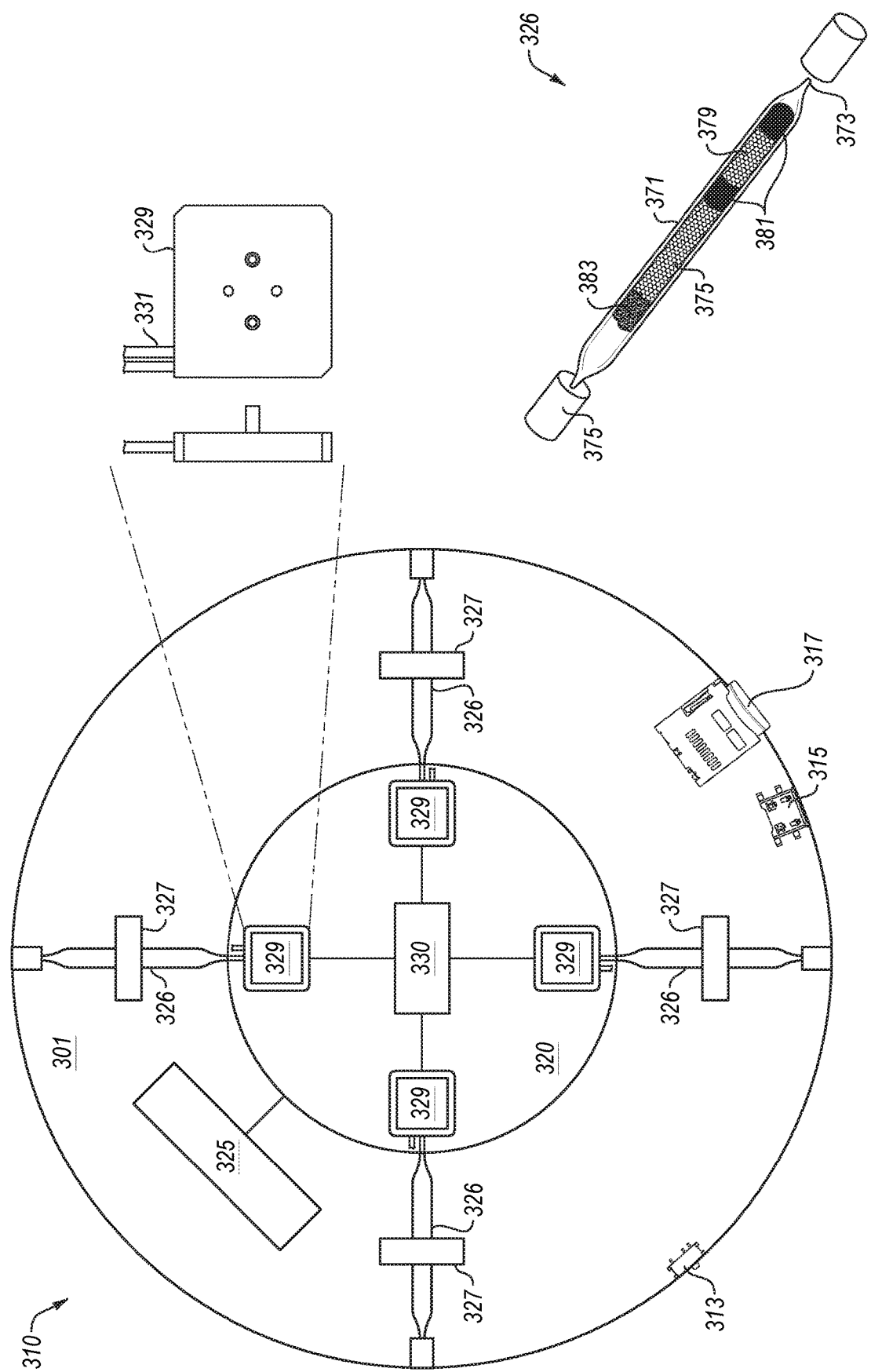
FIG. 3A is a top, plan view of a detector disc that employs a sorbent tube to gather chemical gas contaminants according to aspects of the disclosure.
FIG. 3B is a sorbent tube according to an aspect of the disclosure.

FIG. 3A is a top, plan view of a detector disc 310 that employs a sorbent tube 326 to gather chemical gas contaminants according to aspects of the disclosure. FIG. 3B is a sorbent tube 326 according to an aspect of the disclosure. The sorbent tube 326 includes a glass tube 371 with sealing caps 375 at either end. The glass tube 371 is drawn to very close tolerances for repeatable results. The glass tube 371 includes precision-sealed tips 373, which permit safe, easy breaking to the specified opening size and sealing caps 375, which prevent contamination and to seal the glass tube 371 shut. Inside the glass tube 371 is disposed a sorbent layer 377, which has a precisely controlled surface area, pore size, absorptive characteristics, and mesh size. Also disposed in the glass tube 371 is a backup sorbent layer 379, which detects sample breakthrough. The sorbent layers 377 and 379 include foam separators 381 to provide a uniform pressure drop within the glass tube 371. Also inside the glass tube 371 is disposed a precise amount of a high-purity glass wool 383 also to provide a uniform pressure drop.

With continued referenced to FIG. 3A, in various embodiments, the detector disc 310 includes a substrate disc 301 and an optional printed circuit board (PCB) 320. In some embodiments, the detector disc 310 includes one or more sorbent tube 326 attached to the substrate 301, e.g., with the use of a clamp 327 or other connector (e.g., a glue, bonding agent, clip, magnet, etc.). The detector disc 310 may also include a battery 325 attached to the substrate disc 301 to provide power to the PCB 320 and electronics disposed thereon. The electronics may include, for example, a toggle on/off switch 313, a USB interface connector 315, and a memory card 317 disposed on the PCB 320. A microcontroller 330 may be disposed on one of the substrate disc 301 or the PCB 320. These components are similar to those introduced and discussed with reference to detector disc 110 of FIGS. 2A-2E.

In various embodiments, the electronics include one or more micro-electromechanical system (MEMS) pump 329 disposed on the PCB 320. In an alternative embodiment, although not illustrated, the MEMS pump 329 is disposed on the substrate disc 301. Each MEMS pump 329 includes an air tube 331 attached to an opening of the sorbent tube 326. The MEMS pump 329 is adapted to force ambient air into the sorbent tube 326, e.g., through the air tube 331, and may be programmed or configured to automatically shut off after a calibrated time period after activation. Alternatively, the MEMS pump 329 may shut off responsive to a shutoff signal (e.g., which may be wireless received from a controller) or may be shut off responsive to a sensor reading. For example, a sensor may detect a volume of gas pumped into a sorbent tube 326, and the MEMS pump 329 may be shut off responsive to the volume of gas meeting a threshold. In various embodiments, the ambient air is ambient air of at least one of a storage location, the factory interface 91, the load lock 104a or 104b, the transfer chamber 106, or one of the processing chambers 107 of the substrate processing system 100.

The microcontroller 330 may be a programmed processor, a FPGA, an application-specific integrated circuit (ASIC) or other controller. The microcontroller 330 may be configured to activate the MEMs pump 329, e.g., after detection of movement of the detector disc 301 or some other trigger and/or to shut off the MEMS pump 329, e.g., responsive to a timer timing out, responsive to an external signal, responsive to a measurement from a sensor (e.g., that indicates an amount of gas pumped into a sorbent tube), or responsive to some other condition.

In further embodiments, the detector disc 310 includes at least a second sorbent tube attached to the substrate disc 301, the second sorbent tube including an opening at a first end that is capped and a second opening at a second end that is not capped. A second MEMS pump is disposed on the PCB 320 and that includes a second air tube attached to the second opening of the second sorbent tube to force ambient air into the second sorbent tube. The second MEMS pump may be adapted to automatically shut off after the calibrated time period after activation, and the microcontroller 330 further coupled to the second MEMS pump to activate the second MEMS pump.

Figure 4:
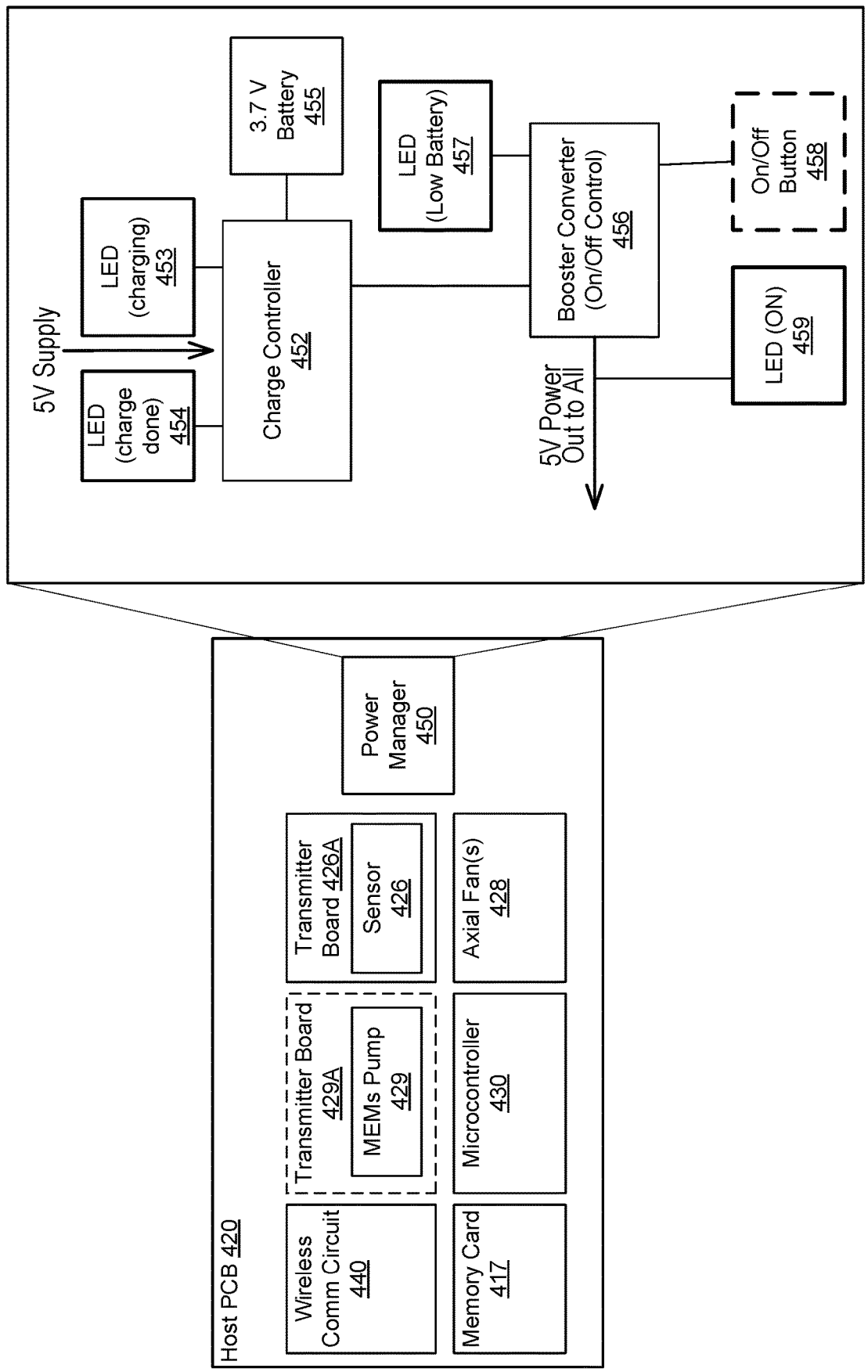
FIG. 4 is a block schematic diagram of a host printed circuit board (PCB) for the detector disc according to aspects of the disclosure.

FIG. 4 is a block schematic diagram of a host printed circuit board (PCB) 420 for the detector disc 110 or 310 according to aspects of the disclosure. The host PCB 420 may therefore be the PCB 220 or PCB 320 in different embodiments, may be a combination of printed circuit boards, and have a number of similar electrical components disposed thereon. For example, the host PCB 420 may include a memory card 417 to store data, a sensor 426 (e.g., solid state sensor) disposed on a transmitter board 426A, one or more axial fan 428, a MEMS pump 429 disposed on a transmitter board 429A, a microcontroller 430, a wireless communication circuit 440, and a power manager 450. As with the detector discs 110 and 310, the PCB 420 may include multiple MEMS pumps 429, each on its own transmitter board 429A, and multiple sensors 426, each on its own transmitter board 426A. Each of the one or more axial fans 428 may be disposed in proximity or adjacent to one of the sensors 426.

In various embodiments, the wireless communication circuit 440 is adapted to transmit wirelessly, e.g., to the WAP 129, either or both of the detection signals (received from the one or more sensor 426) or measurement data that includes the detection signal after conditioning and processing, as will be discussed in more detail with reference to FIG. 6. The wireless communication circuit 440 and the WAP 129, and other wireless enabled devices, may communicate using one or more of various communication standards or protocols such as WiFi™ of the WiFi™ Alliance, Wireless USB®, Bluetooth®, Zigbee®, secure shell (SSH), internet-of-thing (IoT) gateway, or the like.

In various embodiments, the transmitter board 429A on which is disposed the MEMS pump 429 transmits signals between the MEMS pump 429 and the microcontroller 430. The transmitter board 426A on which is disposed the sensor 426 may transmit signals between the sensor 426 and the microcontroller 430.

In one embodiment, the measurement data is stored on the memory card 417. The memory card 417 may be removable for insertion into a memory card reader or the like on a computing device in order to extract the measurement data.

In various embodiments, the power manager 450 is adapted to convert power from the battery 225 or 325 into a proper power and current level for the electrical components disposed on the host PCB 420. For example, the power manager 450 receives a five volt power supply at a charge controller 452 with which to charge a 3.7 volt battery 455. A first light emitting diode (LED) 453 may indicate whether the 3.7 volt battery 455 is charging and a second LED 454 may indicate when the charging is done. The 3.7 volts may be sufficient for some of the components disposed on the host PCB 420, such as the PCB 420, transmitter boards 426A and 429A, and the axial fan(s) 428.

In these embodiments, the power manager 450 may also include a booster converter 456 coupled to the charge controller 452 and adapted to boost a voltage source of the battery to a level (e.g., five volts) sufficient to power at least the microcontroller 430, the sensor 426, and the memory card 417. A third LED 457 may indicate a low power level of the battery 225 or 325 and a fourth LED 459 may indicate that the detector disc 110 or 310 is on. The power manager 450 may also include an on/off button 458 in order cycle on or off the power to the host PCB 420.

Figure 5:
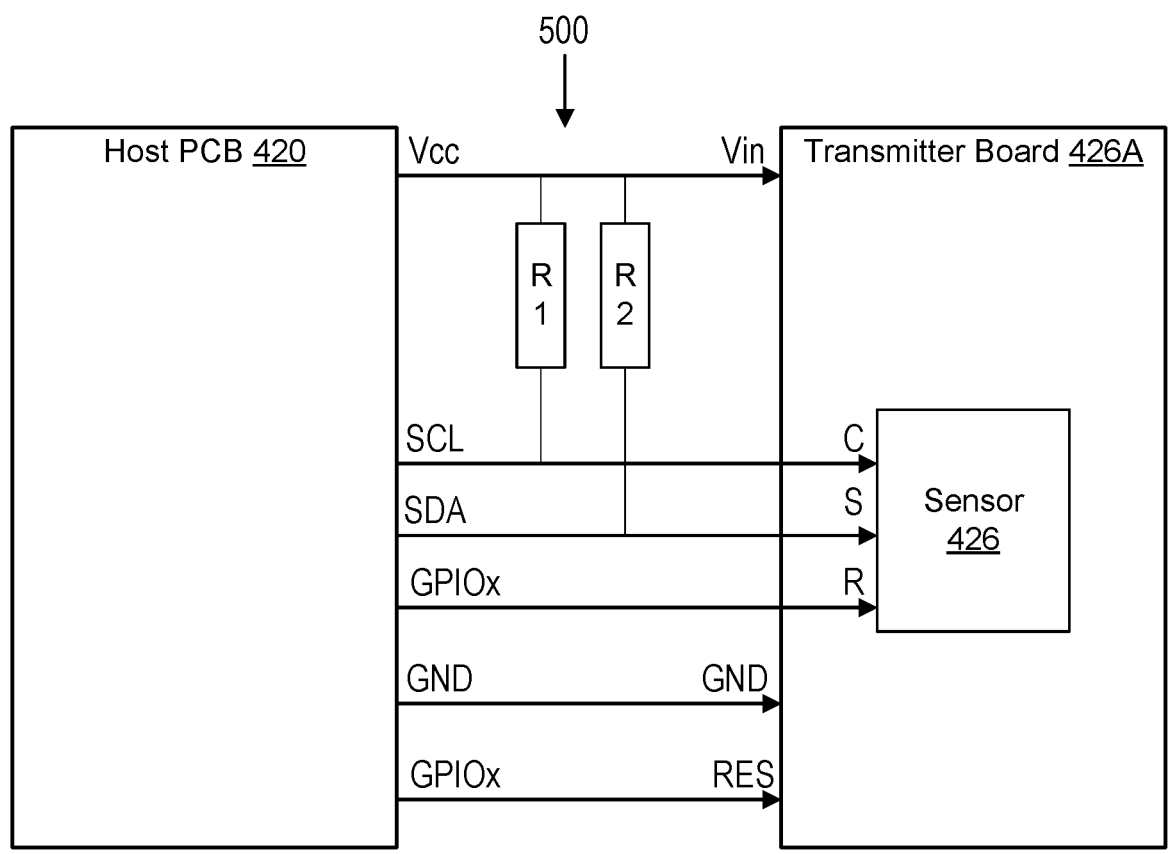
FIG. 5 is a block schematic diagram of a serial communication interface between the host PCB and a transmitter board that includes a sensor according to aspects of the disclosure.

FIG. 5 is a block schematic diagram of a serial communication interface 500 between the host PCB 420 and a transmitter board 426A that includes the sensor 426 according to aspects of the disclosure. In various embodiments, the serial communication interface 500 is an inter-integrated circuit interface (e.g., I2C or I²C), a serial peripheral interface (SPI), or an asynchronous serial interface, or the like. The inter-integrated circuit (I²C) protocol is a protocol intended to allow multiple "slave" digital integrated circuits ("chips") to communicate with one or more "master" chips. In the present disclosure, the microcontroller 230, 330, 430 may be such a master and each of the sensors 226, 426 may be such a slave. In alternative embodiments, a parallel connection is used.

The serial communication interface 500 may include a first resistor (R1) between a Vcc/Vin power line and a serial clock line (SCL) and a second resistor (R2) between the Vcc/Vin power line and a serial data line (SDA). The serial clock line may be a clock (C) input into the sensor 426 and the serial data line may be a data line (S) input into the sensor 426. A general purpose input/output (GPIOx) line may be a receiver mode (R) input from the host PCB 420 to the sensor 426. Another GPIOx input connects to a reset switch (RES). In this way, the host PCB 420 can carry clock, data, mode, and reset signals from on-board components, including the microcontroller 430. In embodiments, the detection signals of levels of the chemical gas contaminants may be transmitted over the serial data line (SDA) through the host PCB 420 and to additional signal processing components for conversion to measurement data.

Figure 6:
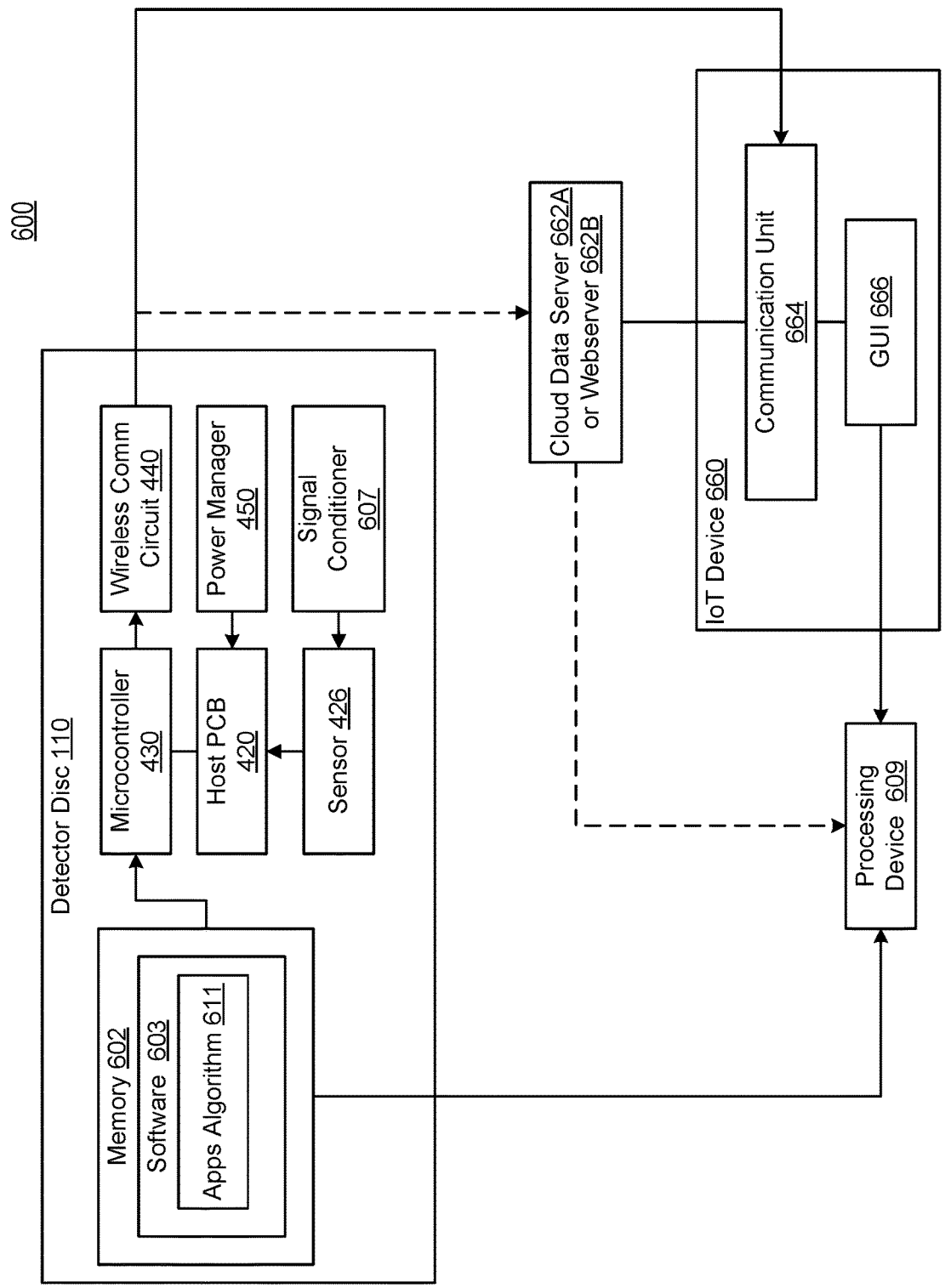
FIG. 6 is a schematic block diagram illustrative of a method for converting detection signals into measurement data for detected levels of chemical gas contaminants and securely transmitting the measurement data according to aspects of the disclosure.

FIG. 6 is a schematic block diagram illustrative of a method 600 for converting detection signals into measurement data for detected levels of chemical gas contaminants and securely transmitting the measurement data according to aspects of the disclosure. In various embodiments, the microcontroller 430 of the detector disc 110 can retrieve instructions from a memory 602, and execute the instructions to perform signal conversion as will be discussed. The microcontroller 430 may execute control over detection signals generated by the sensor 426, e.g., via connections of the host PCB 420, where the detection signals reflect detected levels of the chemical gas contaminants as discussed earlier. The detection signals may be thought of as raw detection data.

The detector disc 110 may further include a signal conditioner 607, which is on board the microcontroller 430 or may be a separate processing components on the host PCB 420. The signal conditioner 607 may power condition the detection signals to generate conditioned analog signals capable of being transferred over longer flex cables.

In various embodiments, the microcontroller 430 executes software 603 (e.g., software code or instructions retrieved from the memory 602) to process the conditioned analog signals into measurement data that may be transmitted and processed for user consumption. In one embodiment, the memory 602 is memory card 217 or 417. In another embodiment, the conditioned analog signals are transmitted to another device such as the controller 109 (or other networked device) that can perform the software processing. In one embodiment, the microcontroller 430 includes an analog-to-digital converter (ADC) to convert the conditioned detection signals into digital detection data that can then be measured. For example, the microcontroller 430 can further execute an applications algorithm 611 to convert the digital detection data into the measurement data associated with discrete values (e.g., in ppm) of the detected levels of the chemical gas contaminants.

After the microcontroller 430 executes the software 603, the wireless communication circuit 440 may transmit the measurement data to an internet-of-things (IoT) device 660, which may act as an IoT gateway for storing the measurement data to a cloud data server 662A and/or a webserver 662B. If the controller 109 (or other network-enabled computing device) executes the software 603, the controller 109 (or other network-enable computing device) may send the measurement data to the IoT device 660. The IoT device 660 may provide a secure gateway or router for transmitting the measurement data to be stored at the cloud data server 662A and/or the webserver 662B. The measurement data may be securely stored at either or both of the cloud data server 662A and/or the webserver 662B, and accessed by a processing device 609. In an alternative embodiments (indicated with the dashed line) the wireless communication circuit 440 transmits the measurement data directly to the cloud data server 662A or the webserver 662B.

In various embodiments, the IoT device 660 may include a communication unit 664, e.g., that includes a transceiver to store to and retrieve the measurement data from the cloud data server 662A and/or the webserver 662B. The IoT device 660 may further include a graphical user interface (GUI) 666 with which a processing device 609 can interact to receive and review the measurement data in a human accessible form. The processing device 609 may be a client device, a computing device, a mobile device, or the like. In some embodiments, the processing device 609 can directly access the measurement data from the cloud data server 662A and/or the webserver 662B.

In various embodiments, the network communications between the detector disc 110, the controller 109, the cloud data server 662A and/or webserver 662B, and the processing device 609 may be secured via security protocols, to include verification, authentication, and encryption, or a combination of the same. In one embodiment, all of these devices are co-located on a single local area network (LAN) that has not outside connection to the internet (or other wide area network), and is secured by being physically separate from other computer networks.

Figure 7:
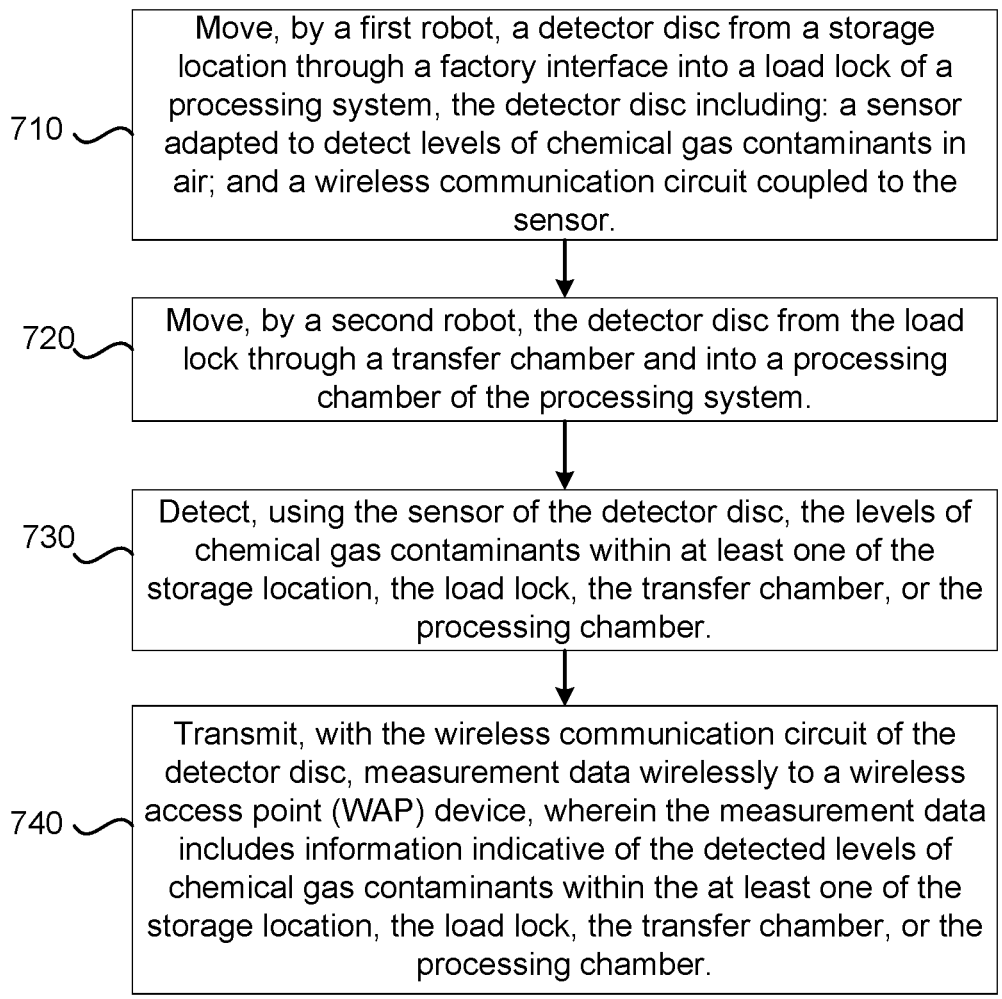
FIG. 7 is a flow chart of a method for using a detector disc, which includes a sensor for detecting levels of chemical gas contaminants according various aspects of the disclosure.

FIG. 7 is a flow chart of a method 700 for using a detector disc, which includes a sensor for detecting levels of chemical gas contaminants according various aspects of the disclosure. For example, the method 700 may be implemented using the detector disc 110 in conjunction with the factory interface robot 111 (first robot) and the transfer chamber robot 112 (second robot).

With reference to FIG. 7, at operation 710, the first robot moves the detector disc 110 from a storage location through a factory interface into a load lock of a processing system 100, where the detector disc includes a sensor adapted to detect levels of chemical gas contaminants in air; and a wireless communication circuit coupled to the sensor. The sensor may be a solid state sensor or a micro solid state sensor.

At operation 720, the second robot moves the detector disc 110 from the load lock through a transfer chamber and into a processing chamber of the processing system. At operation 730, the sensor detects the levels of chemical gas contaminants within at least one of the storage location, the factory interface, the load lock, the transfer chamber, or the processing chamber.

With continued reference to FIG. 7, the detector disc 110 transmits, with the wireless communication circuit of the detector disc, measurement data wirelessly to a wireless access point (WAP) device. The measurement data may include information indicative of the detected levels of chemical gas contaminants within the at least one of the storage location, the factory interface, the load lock, the transfer chamber, or the processing chamber.

Similar or corresponding operations may be performed during a return trip to the storage location. For example, the second robot can move the detector disc from the processing chamber through the transfer chamber and back into the load lock of the processing system. The first robot may move the detector disc from the load lock through the factory interface and back into the storage location of the processing system. The sensor of the detector disc may detect the levels of chemical gas contaminants within at least one of the processing chamber, the transfer chamber, the load lock, the factory interface, or the storage location during a return trip of the detector disc to the storage location. The wireless communication circuit of the detector disc can further transmit second measurement data wirelessly to the WAP device. The second measurement data may include information indicative of the levels of chemical gas contaminants within the at least one of the processing chamber, the transfer chamber, the load lock, the factory interface, or the storage location on the return trip.

Figure 8:
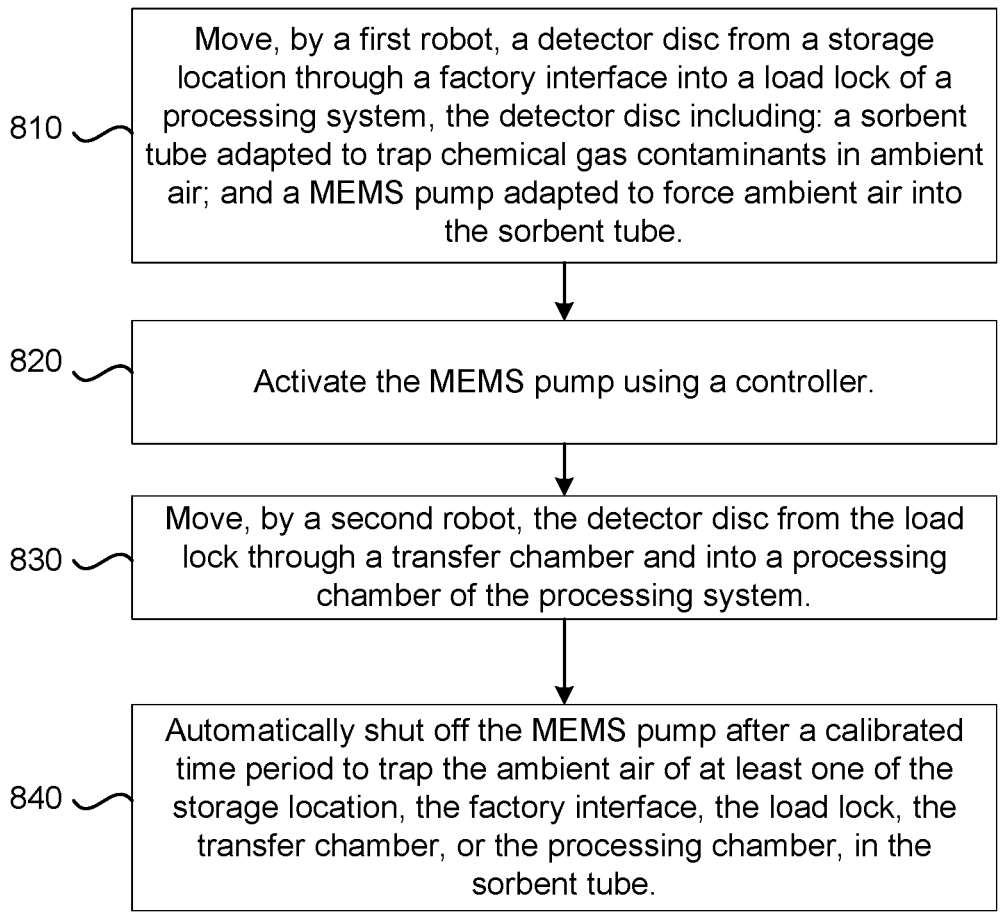
FIG. 8 is a flow chart of a method for using a detector disc, which includes a sorbent tube, for detecting levels of chemical gas contaminants according various aspects of the disclosure.

FIG. 8 is a flow chart of a method 800 for using a detector disc, which includes a sorbent tube, for detecting levels of chemical gas contaminants according various aspects of the disclosure. For example, the method 700 may be implemented using the detector disc 310 in conjunction with the factory interface robot 111 (first robot) and the transfer chamber robot 112 (second robot).

With reference to FIG. 8, at operation 810, the first robot moves the detector disc 310 from a storage location through a factory interface into a load lock of a processing system, where the detector disc includes a sorbent tube adapted to trap chemical gas contaminants in ambient air, and a MEMS pump adapted to force the ambient air into the sorbent tube.

At operation 820, a controller such as the microcontroller 330 activates the MEMS pump on the detector disc 310, e.g., upon detecting movement through the processing system 100 or in response to anther trigger, such as a command signal. At operation 830, the second robot moves the detector disc 310 from the load lock through the transfer chamber and into a processing chamber of the processing system 100.

At operation 840, the controller automatically shuts off the MEMS pump after a calibrated time period to trap the ambient air of at least one of the storage location, the load lock, the factory interface, the transfer chamber, or the processing chamber, in the sorbent tube. Because the detector disc 310 has multiple sorbent tubes, a separate sorbent tube may be activated within each one of these different tool locations in order to isolate the ambient air in respective sorbent tube to particular parts or areas of the processing system 100.

The preceding description sets forth numerous specific details such as examples of specific systems, components, methods, and so forth, in order to provide a good understanding of several embodiments of the present invention. It will be apparent to one skilled in the art, however, that at least some embodiments of the present invention may be practiced without these specific details. In other instances, well-known components or methods are not described in detail or are presented in simple block diagram format in order to avoid unnecessarily obscuring the present invention. Thus, the specific details set forth are merely exemplary. Particular implementations may vary from these exemplary details and still be contemplated to be within the scope of the present invention.

Reference throughout this specification to "one embodiment" or "an embodiment" means that a particular feature, structure, or characteristic described in connection with the embodiment is included in at least one embodiment. Thus, the appearances of the phrase "in one embodiment" or "in an embodiment" in various places throughout this specification are not necessarily all referring to the same embodiment. In addition, the term "or" is intended to mean an inclusive "or" rather than an exclusive "or." When the term "about" or "approximately" is used herein, this is intended to mean that the nominal value presented is precise within ±10%.

Although the operations of the methods herein are shown and described in a particular order, the order of the operations of each method may be altered so that certain operations may be performed in an inverse order or so that certain operation may be performed, at least in part, concurrently with other operations. In another embodiment, instructions or sub-operations of distinct operations may be in an intermittent and/or alternating manner. In one embodiment, multiple metal bonding operations are performed as a single step.

It is to be understood that the above description is intended to be illustrative, and not restrictive. Many other embodiments will be apparent to those of skill in the art upon reading and understanding the above description. The scope of the invention should, therefore, be determined with reference to the appended claims, along with the full scope of equivalents to which such claims are entitled.

What is claimed is:

1. A detector disc comprising:
a disc body comprising a bottom disc and a top cover, the top cover comprising a first aperture and a sidewall that is attached to the bottom disc;
a sensor disposed within an interior formed by the disc body and positioned to be exposed to an external environment via the first aperture in the top cover, wherein the sensor is adapted to detect levels of chemical gas contaminants and output a detection signal based on detected levels of the chemical gas contaminants;
a microcontroller disposed within the interior of the disc body and coupled to the sensor, the microcontroller adapted to generate measurement data from the detected levels of the chemical gas contaminants embodied within the detection signal; and
a wireless communication circuit disposed within the interior of the disc body and coupled to the microcontroller, the wireless communication circuit adapted to transmit the measurement data wirelessly to a wireless access point device.

2. The detector disc of claim 1, wherein the sensor is adapted to detect the levels of chemical gas contaminants in parts per million of particles of at least one of airborne molecular contaminants or volatile organic compounds.

3. The detector disc of claim 1, wherein the sensor is a solid state sensor that is to:
measure fifty percent of a concentration of the levels of the chemical gas contaminants within 10 seconds; and
measure ninety percent of the concentration of the levels of the chemical gas contaminants within 30 seconds.

4. The detector disc of claim 1, further comprising a printed circuit board (PCB) disposed within the interior of the disc body and on which is disposed at least the sensor, wherein the bottom disc comprises a substrate and the sidewall encloses the PCB, the sidewall comprising at least one opening to provide access to connector interfaces attached to the PCB.

5. The detector disc of claim 1, further comprising:
a printed circuit board (PCB) disposed within the interior of the disc body and on which is disposed at least the sensor; and
a serial communication interface that couples the sensor to the PCB, the serial communication interface to transmit the detection signal from the sensor to the PCB, and wherein the serial communication interface is one of a serial peripheral interface or an inter-integrated circuit interface.

6. The detector disc of claim 1, wherein the top cover comprises a second aperture located proximate to the first aperture, the detector disc further comprising:
a printed circuit board (PCB) disposed within the interior of the disc body and on which is disposed at least the sensor; and
an axial fan disposed on the PCB beneath the second aperture, wherein the axial fan is to move air across the sensor.

7. The detector of claim 6, wherein the PCB comprises a third aperture positioned below the second aperture and the axial fan is disposed on the PCB between the second and third apertures to move air across the sensor in through the second aperture and out through the third aperture of the PCB.

8. The detector disc of claim 1, further comprising a printed circuit board (PCB) disposed within the interior of the disc body and on which is disposed at least the sensor, wherein the top cover comprises a set of first apertures, which include the first aperture, and wherein the detector disc further comprises a set of sensors disposed on the PCB, the set of sensors comprising the sensor, wherein each sensor of the set of sensors is positioned proximate to one of the set of first apertures.

9. The detector disc of claim 8, wherein the top cover comprises a set of second apertures proximate to the set of first apertures and the PCB comprises a set of third apertures positioned below the set of second apertures, and wherein the detector disc further comprises a set of axial fans disposed on the PCB between the set of second apertures and the set of third apertures, the set of axial fans to move air across the set of sensors.

10. The detector disc of claim 1, further comprising:
a printed circuit board (PCB) disposed within the interior of the disc body, wherein the sensor, the microcontroller, and the wireless communication circuit are disposed on the PCB;
a memory card disposed on the PCB, the memory card to store the measurement data;
a battery disposed on the PCB; and
a power manager coupled to the battery, the power manager comprising a booster converter to convert a voltage source of the battery to a power level sufficient to power at least the microcontroller, the sensor, and the memory card.

11. The detector disc of claim 1, wherein a thickness of the disc body is between 6 millimeters (mm) and 9 mm, and wherein a diameter of the disc body is approximately 190 mm to 320 mm.

12. A detector disc comprising:
a substrate disc;
a sorbent tube attached to the substrate disc, the sorbent tube comprising a first opening at a first end that is capped and a second opening at a second end;
a micro-electromechanical system (MEMS) pump disposed the substrate disc, the MEMS pump comprising an air tube attached to the second opening of the sorbent tube to force ambient air into the sorbent tube, wherein the MEMS pump is to automatically shut off after a calibrated time period after activation; and
a microcontroller disposed on the substrate disc and coupled to the MEMS pump, the microcontroller to activate the pump.

13. The detector disc of claim 12, wherein a thickness of the detector disc is between 6 millimeters (mm) and 9 mm, and wherein the sorbent tube is attached to the substrate disc with a clamp.

14. The detector disc of claim 12, further comprising:
a printed circuit board (PCB) disposed on a central portion of the substrate disc, wherein the MEMS pump and the microcontroller are disposed on the PCB;
a second sorbent tube attached to the substrate disc, the second sorbent tube comprising a third opening at a first end that is capped and a fourth opening at a second end; and
a second MEMS pump disposed on one of the substrate disc or the PCB and comprising a second air tube attached to the fourth opening of the second sorbent tube to force ambient air into the second sorbent tube, wherein the second MEMS pump is to automatically shut off after the calibrated time period after activation; and wherein the microcontroller is further coupled to the second MEMS pump, the microcontroller further to activate the second MEMS pump.

15. The detector disc of claim 12, wherein the ambient air is ambient air of at least one of a storage location, a factory interface, a load lock, a transfer chamber, or a processing chamber of a substrate processing system.

16. A method comprising:

moving, by a first robot, a detector disc from a storage location through a factory interface into a load lock of a processing system, the detector disc comprising:
a sensor adapted to detect levels of chemical gas contaminants in air; and
a wireless communication circuit coupled to the sensor;
moving, by a second robot, the detector disc from the load lock through a transfer chamber and into a processing chamber of the processing system;
detecting, using the sensor of the detector disc, the levels of chemical gas contaminants within at least one of the storage location, the factory interface, the load lock, the transfer chamber, or the processing chamber; and
transmitting, with the wireless communication circuit of the detector disc, measurement data wirelessly to a wireless access point (WAP) device, wherein the measurement data comprises information indicative of the detected levels of chemical gas contaminants within the at least one of the storage location, the factory interface, the load lock, the transfer chamber, or the processing chamber.

17. The method of claim 16, wherein transmitting comprises at least one of:
transmitting a first portion of the measurement data to the WAP device while the detector disc is in the storage location;
transmitting a second portion of the measurement data to the WAP device while the detector disc is in the factory interface;
transmitting a third portion of the measurement data to the WAP device while the detector disc is in the load lock;
transmitting a fourth portion of the measurement data to the WAP device while the detector disc is in the transfer chamber; and
transmitting a fifth portion of the measurement data to the WAP device while the detector disc is in the processing chamber.

18. The method of claim 16, further comprising:
moving, by the second robot, the detector disc from the processing chamber through the transfer chamber and back into the load lock of the processing system;
moving, by the first robot, the detector disc from the load lock through the factory interface and back into the storage location of the processing system;
detecting, using the sensor of the detector disc, the levels of chemical gas contaminants within at least one of the processing chamber, the transfer chamber, the load lock, the factory interface, or the storage location during a return trip of the detector disc to the storage location; and
transmitting, with the wireless communication circuit, second measurement data wirelessly to the WAP device, wherein the second measurement data comprises information indicative of the levels of chemical gas contaminants within the at least one of the processing chamber, the transfer chamber, the load lock, the factory interface, or the storage location on the return trip.

19. The method of claim 16, further comprising calibrating the sensor within air located outside a factory interface that includes the storage location, wherein the calibrating comprising establishing a baseline of levels of the chemical gas contaminants detected by the sensor.

20. The method of claim 16, further comprising:
receiving a detection signal, from the sensor, indicative of the detected levels of chemical gas contaminants;
conditioning, using a signal conditioner, the detection signal to generate a conditioned analog signal;
converting, using an analog-to-digital converter, the conditioned analog signal to a digital signal; and
converting the digital signal to generate the measurement data via measuring discrete values of the detected levels of chemical gas contaminants within the digital signal.

\* \* \* \* \*

UNITED STATES PATENT AND TRADEMARK OFFICE
CERTIFICATE OF CORRECTION

| | | |
|---|---|---|
| PATENT NO. | : 11,353,381 B1 | |
| APPLICATION NO. | : 16/946195 | |
| DATED | : June 7, 2022 | |
| INVENTOR(S) | : Devendra Channappa Holeyannavar et al. | |

It is certified that error appears in the above-identified patent and that said Letters Patent is hereby corrected as shown below:

In the Specification

In Column 5, Line 50, after "and" insert --9--

In Column 6, Line 13, replace "concertation" with --concentration--

In Column 7, Line 2, after "one" insert --or--

In the Claims

In Claim 12, Column 14, Line 43, before "the substrate disc" insert --on--

Signed and Sealed this
Thirty-first Day of January, 2023

Katherine Kelly Vidal
*Director of the United States Patent and Trademark Office*